(12) United States Patent
Haueter et al.

(10) Patent No.: US 7,985,203 B2
(45) Date of Patent: Jul. 26, 2011

(54) SEQUENTIAL INTRODUCTION OF SKIN PENETRATORS

(75) Inventors: Ulrich Haueter, Grosshochstetten (CH); Sandro Niederhauser, Bleienbach (CH); Peter Feldmann, Krauchthal (CH); Christian Hof, Bern (CH)

(73) Assignee: Roche Diagnostics International AG, Steinhaunsen (CH)

( * ) Notice: Subject to any disclaimer, the term of this patent is extended or adjusted under 35 U.S.C. 154(b) by 296 days.

(21) Appl. No.: 11/847,857

(22) Filed: Aug. 30, 2007

(65) Prior Publication Data

US 2008/0140009 A1 Jun. 12, 2008

Related U.S. Application Data

(63) Continuation of application No. PCT/EP2006/001715, filed on Feb. 24, 2006.

(30) Foreign Application Priority Data

Mar. 4, 2005 (EP) .................................... 05004760

(51) Int. Cl.
*A61M 5/00* (2006.01)
*A61B 17/14* (2006.01)
*A61B 17/32* (2006.01)

(52) U.S. Cl. ........................ 604/158; 606/182
(58) Field of Classification Search .................. 600/365; 604/159–162; 606/181–183
See application file for complete search history.

(56) References Cited

U.S. PATENT DOCUMENTS

| 5,299,571 A * | 4/1994 | Mastrototaro ............... 600/347 |
| 2005/0033341 A1 | 2/2005 | Vreeke et al. |

FOREIGN PATENT DOCUMENTS

| JP | 2000217804 | 8/2000 |
| WO | 03080169 A1 | 10/2003 |
| WO | WO 03/080169 A1 | 10/2003 |
| WO | 04069035 A2 | 8/2004 |
| WO | WO 2004/069035 A2 | 8/2004 |
| WO | WO 2005/044116 | 3/2005 |
| WO | 05044116 A1 | 5/2005 |

OTHER PUBLICATIONS

Patent Abstracts of Japan, vol. 2000, No. 11, Jan. 3, 2001 & JP 2000 217804 a (KDK Corp.), Aug. 8, 2000.

* cited by examiner

*Primary Examiner* — Nicholas D Lucchesi
*Assistant Examiner* — Rebecca E Eisenberg
(74) *Attorney, Agent, or Firm* — Dinsmore & Shohl LLP (57) ABSTRACT

A device for facilitating the use or application of skin penetrators, the device including a puncturing part for piercing the skin, an indwelling part which can be introduced into the skin through an opening generated by the puncturing part and remains there, wherein the puncturing part and indwelling part are operably associated with the device, and a guide operably associated with the device, wherein, in use, the indwelling part is moved, via the guide, into a position of use after the puncturing part has pierced the skin. In some embodiments, the puncturing and indwelling parts are separate from each other prior to use. A method of using skin penetrators is encompassed and includes sequentially introducing the puncturing part and the indwelling part into the skin.

24 Claims, 11 Drawing Sheets

SEQUENTIAL INTRODUCTION OF SKIN PENETRATORS

CROSS-REFERENCE TO RELATED APPLICATION(S)

This application is a continuation of International Application No. PCT/EP2006/001715, filed on Dec. 24, 2006, which claims priority to German Application No. 05 004 760.4, filed on Mar. 4, 2005, the contents of both of which are incorporated in their entirety herein by reference.

BACKGROUND

The present invention relates to devices for injecting, infringing, administering, delivering and dispensing substances, and to methods for making and using such devices, as well as to related peripheral, adjunct, complementary, cooperative and auxiliary devices and methods. More particularly, the present invention relates to the sequential application or use of skin penetrators. In the context of the present invention, the expression "skin penetrators" signifies devices that are introduced through the skin into the body from outside the body. For example, these can be cannulas for administering medicaments, probes that are inserted into the skin or into the underlying tissue, or sensors for measuring a physiological parameter, such as glucose sensors.

Elements of such devices are a puncturing part, which pierces the skin, and an indwelling part, which is introduced into a skin opening or channel formed by the puncturing part and remains there. Known designs have a relatively soft cannula, which is made of plastic material and which forms the indwelling part, and a steel cannula, which is provided with a tip and which extends through the plastic cannula, the tip protruding from the front of the plastic cannula. Upon application or in the use of these known designs, the puncturing part and indwelling part are inserted together, after which the steel cannula is withdrawn from the plastic cannula, such that only the plastic cannula remains in the body. The plastic cannula is attached to a line system (in most cases via an adapter, which can also serve as a guide for the steel cannula) to allow liquid to flow in or out through the skin.

Disadvantages of known systems of this kind include the following: the steel cannula has to be removed and disposed of in a separate operating step. If it remains in the body during the wearing period, it is found to be uncomfortable or painful. The geometry of the cutting edge for the tip of the steel cannula must protrude from the plastic cannula and thus increases the overall length by several millimetres. Introducing the steel cannula into the plastic cannula during the manufacture of the system proves difficult if the soft plastic cannula is even just slightly bent. The plastic cannula could then be damaged or destroyed by the tip of the steel cannula.

SUMMARY

An object of the present invention is to make available a device for facilitating the use or application of skin penetrators and which addresses the abovementioned disadvantages of known designs. Another object is to make available an applicator device for skin penetrators, which applicator device is easy to handle, is well tolerated and functions well.

Thus, in one embodiment, the present invention comprises a device for facilitating the use or application of skin penetrators, the device comprising a puncturing part for piercing the skin, an indwelling part which can be introduced into the skin through an opening generated by the puncturing part and remains there, wherein the puncturing part and indwelling part are operably associated with the device, and a guide operably associated with the device, wherein, in use, the indwelling part is moved in or onto the guide after the puncturing part is moved in or onto the guide.

In one embodiment, the device further comprises a housing carrying the guide, and the guide comprises an abutment for contact by at least one of the puncturing part and the indwelling part, the abutment forming a hold point for at least one of the puncturing part and the indwelling part, wherein the puncturing part and the indwelling part are guided in the guide in a movement that brings the puncturing part into contact with the abutment thereby holding the puncturing part at the hold point, the movement then continuing carrying the indwelling part into a use position. In some embodiments, the puncturing part and the indwelling part may be separate from each other and the device prior to use. In some embodiments, the movement may be a movement in or during at least part of which the puncturing part and the indwelling part are operably coupled.

In one embodiment, the present invention comprises a method for the use of skin penetrators, the method involving a device comprising a puncturing part, which pierces the skin, and an indwelling part, which is introduced into the skin through an opening generated by the puncturing part and remains there, and comprising the step of introducing the puncturing part and the indwelling part into the skin sequentially via a guide associated with the device.

In one embodiment, the present invention comprises a device for facilitating the use or application of skin penetrators, the device including a puncturing part for piercing the skin, an indwelling part which can be introduced into the skin through an opening generated by the puncturing part and remains there, wherein the puncturing part and indwelling part are operably associated with the device, and a guide operably associated with the device, wherein, in use, the indwelling part is moved, via the guide, into a position of use after the puncturing part has pierced the skin. In some embodiments, the puncturing and indwelling parts are separate from each other prior to use. A method of using skin penetrators is encompassed and includes sequentially introducing the puncturing part and the indwelling part into the skin.

In some embodiments, the device for application of skin penetrators according to the present invention is characterized in that the puncturing part and the indwelling part are provided separately on the applicator device, and by at least one guide in or on which the indwelling part is brought after the puncturing part into the puncture position thereof to be introduced into the skin.

Alternatively, the puncturing part and the indwelling part can be mounted on two separate devices or can be designed as two separate devices. A one-part design of the device is one preferred embodiment, i.e. the puncturing part and the indwelling part are component parts of one device.

In some embodiments, the puncturing part and indwelling part are produced and/or provided spatially separately and alongside one another and are introduced sequentially into the skin. The guide ensures that the indwelling part is exactly in a position above the pre-formed hole when it is introduced into the skin. In some embodiments, a device is preferred in which the puncturing part and the indwelling part are arranged in or on a housing.

Advantageously, it is therefore no longer necessary to make the puncturing part longer than the indwelling part. Both parts can be of the same length, such that the skin is not pierced any further or more deeply than is necessary. In some embodiments, a puncturing part is preferred that is less long than the indwelling part, e.g., less than approximately half as long as the puncturing part. In some preferred embodiments, the puncturing part may have a length that is less than approximately one third of the length of the indwelling part.

In some embodiments, a steel needle, which, in some embodiments may be solid, i.e., not hollow, can be used as the mechanical puncturing part. Other types of needles could be used, as well as needles made of other materials.

The provision of the guide assists the user by ensuring that it is not possible to make an error when introducing the indwelling part, e.g., that the channel formed in advance by the puncturing part will be reliably targeted. The puncturing part does not remain in the channel, with the result that the user does not experience discomfort.

According to one embodiment of the present invention, the guide is able to guide the puncturing part and the indwelling part, and it can have a hold point assigned to the puncture position or application (or use or indwelling) position. The puncturing part can, for example, include a puncturing part support on which a puncturing element for opening the skin is mounted.

In some embodiments, the hold point may be formed by an abutment for the puncturing part and/or the indwelling part. Such an abutment has the advantage that it helps provide for positioning accuracy. If an abutment is provided, it is advantageous that the puncturing part and the indwelling part are guided in the guide with coupled movement, and the hold point is generated by an abutment onto which the puncturing part is guided after the puncturing procedure, the continued movement thereby carrying the indwelling part into its application or use position.

The hold point already discussed above can, in principle, be formed by a locking engagement for the puncturing part and/or the indwelling part, the locking engagement being arranged in or on the guide. In this case, it is advantageous if a single releasable locking engagement is provided in or on the guide, into which first the puncturing part and thereafter the indwelling part can lock.

According to a preferred embodiment of the present invention, a retaining member is present on or in the guide and retains the puncturing part in the retracted position (after the preliminary puncture) or holds the coupled unit of the separate puncturing part and indwelling part in the use position of the indwelling part. An advantage lies in the fact that, after the indwelling part has been brought into the application or indwelling use position, no inadvertent displacement can take place, with the result that a precise positioning of the indwelling part over the pre-formed channel is substantially guaranteed.

In a further embodiment, the puncturing part and the indwelling part can be received in a housing in which the guide and the abutment is/are accommodated, the housing having a passage for the puncturing part and the indwelling part. The housing can be adapted such that it facilitates the handling of the entire device and also accommodates or secures additional elements that may be needed or useful.

In a preferred variant of the device according to the present invention, a puncturing part receiver can be arranged on the guide or in the housing to receive the puncturing part, after removal from the puncture position, and to safely stow it away. In some embodiments of the device according to the present invention, the puncturing part is retracted or removed from its position above the pre-formed channel after a piercing operation. If it is guided into the puncturing part receiver described above, the advantages are, on the one hand, that it no longer has to be disposed of and, on the other hand, it no longer poses a risk of injury to the user.

According to an advantageous embodiment of the present invention, an additional or integrated component part in the form of a skin tensioner can be arranged on the guide or on the housing. After the puncturing procedure, it engages on the skin around the channel and holds the channel open, such that the indwelling part can be introduced even more easily.

The above-described guide for the puncturing part and indwelling part can be of any desired configuration. It can be a curved guide, a linear guide or a combination of curved and linear guide. It is advantageously configured such that the piercing movement of the puncturing part and the application movement of the indwelling part can be executed independently of one another, even if the two said parts are otherwise coupled in terms of motion.

In another preferred embodiment of the device according to the present invention, the movements of the puncturing part and of the indwelling part are coupled in such a way that the return movement of the puncturing part partially overlaps the insertion movement of the indwelling part. In some preferred embodiments, this partial overlap involves the puncturing part being withdrawn almost completely from the skin, and only its distal tip still being located in the skin, and overlapping the insertion movement of the indwelling part.

In another advantageous embodiment of the device according to the present invention, the indwelling part is made of a material that has a greater stiffness at ambient or room temperature than it does at body temperature. It is possible, for example, to use plastics that are relatively rigid at a time before introduction of the indwelling part to make it easier to introduce the indwelling part into the skin. This can be achieved using a temperature-sensitive material that is relatively rigid at room temperature or "normal" ambient temperature (about 18 to 24° C.) but becomes relatively soft in the skin, that is to say at body temperature/skin temperature.

In some embodiments, the invention also relates to a method for application or use of skin penetrators with a puncturing part, which pierces the skin, and with an indwelling part, which is introduced into an opening or channel generated in the skin by the puncturing part and remains there. In one embodiment of the method, the puncturing part and the indwelling part, which are provided separately on an applicator device, are introduced sequentially into the skin by a guide. The indwelling part and the puncturing part are brought into the puncture position in or on the guide.

The method has the advantages that have already been described above in connection with the device according to the present invention. When carrying out the method, a device of the kind that has already been described above in various embodiments can be used.

As used in the context of the present application, the expression "puncturing part" includes not only mechanical structures such as needles, for example, but also jets of liquid (which can be used to open the skin), lasers and pyrotechnic devices.

As used in the context of the present application, the expression "sequential introduction" includes not only a complete time separation of the two procedures (insertion of the puncturing part and application (or use, placing or insertion) of the indwelling part), but also procedures in which there is a time overlap between the puncturing procedure and the application procedure, i.e. the two procedures are dephased. A possible overlap entails, for example, that the indwelling part is already introduced into the skin while the puncturing part is being withdrawn from the skin. A further overlap entails that the puncturing part is almost completely retracted from the skin when the indwelling part is being introduced into the skin. This, in some embodiments, the movements of puncturing part and indwelling part are coupled but not identical, i.e. staggered in time.

DETAILED DESCRIPTION

Figure 1:
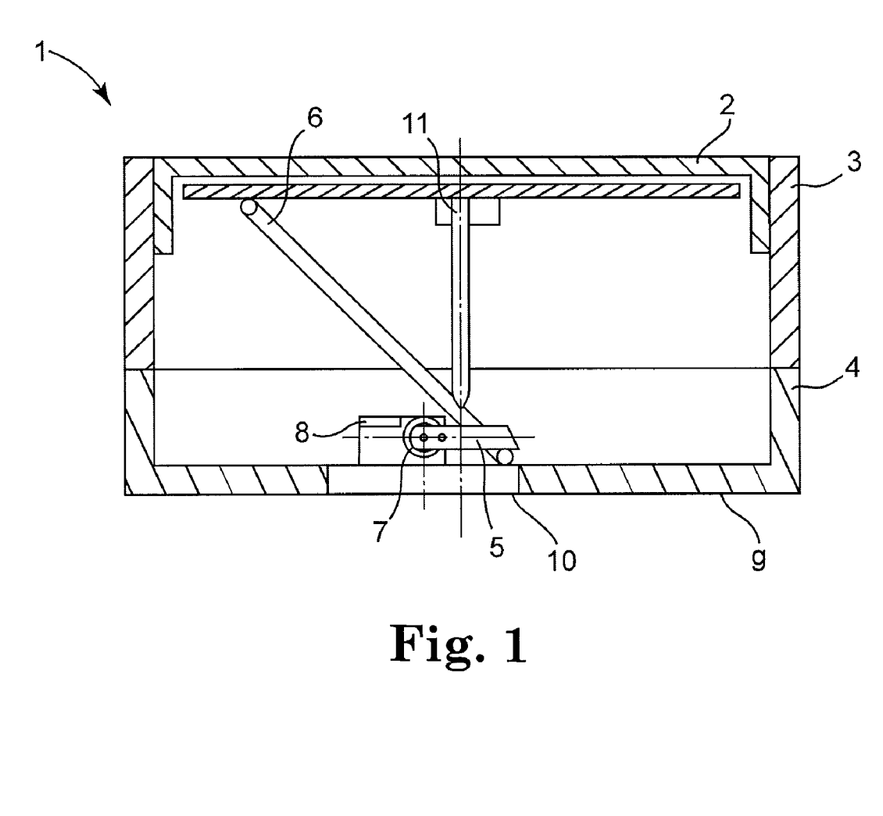
FIG. 1 shows a first embodiment of a device according to the present invention for application or use of skin penetrators, with a rotary blade as a puncturing part, before use.
Figure 2:
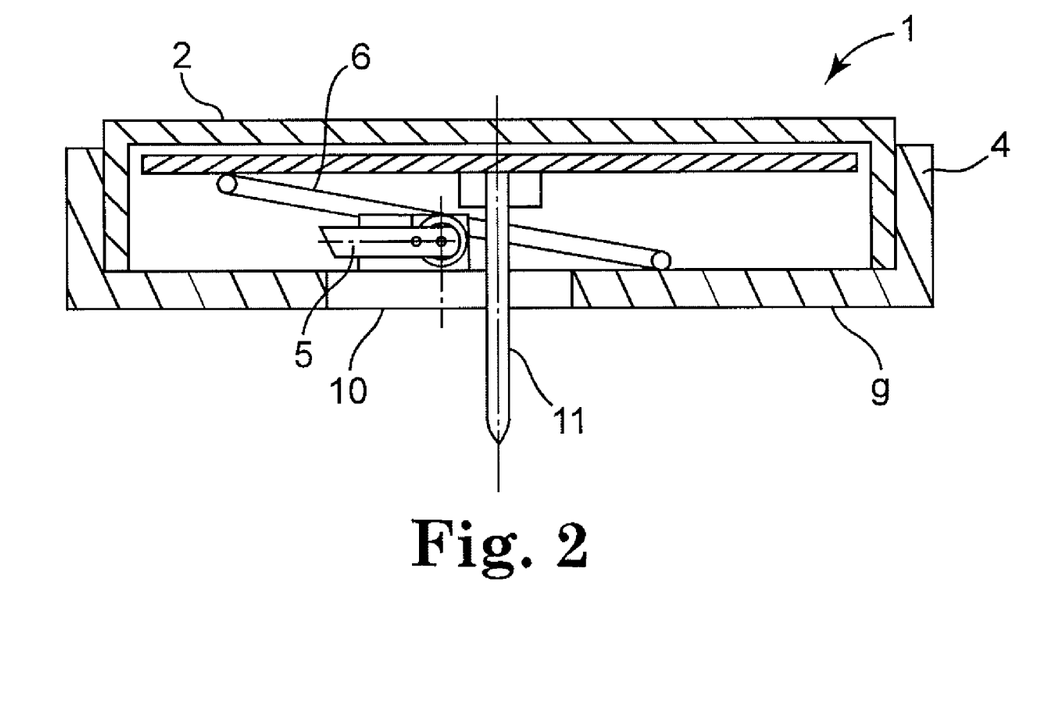
FIG. 2 shows the device of FIG. 1 after its use.

FIGS. 1 and 2 depict one embodiment of a device according to the present invention. The device is for use in the introduction of skin penetrators into the skin, and FIG. 1 shows the device 1 before use, i.e. before introduction of the skin penetrator into or through the skin, and FIG. 2 shows the situation after the skin penerator has been introduced into the subcutaneous tissue.

The housing upper part 2 is connected to the housing lower part 4 by an attachment ring 3. (It should be appreciated that relative and/or positional terms, e.g., upper, lower, top, bottom, etc., are, unless otherwise stated, used for convenience not limitation.) In this example, a rotary blade 5 serves as the puncturing part. Before use, the rotary blade 5 is held in the starting position by a clip 6. A spring 7 serves as the means of driving the rotary blade 5 and, in the starting position illustrated, is tensioned. The underside 9 of the housing 4 is positioned on a skin surface and has an opening 10 in the area of the rotary blade 5, such that a sharp edge of the rotary blade 5 emerges from the housing underside 9 and can pass through or open the skin. The indwelling part 11 is introduced into the skin through the same opening 10.

The rotary blade 5 is arranged in the device in such a way that, upon use of the device, it makes a small incision in the upper layers of the skin, which incision is sufficient to allow the indwelling part 11 to pass through the skin and be positioned in the subcutaneous tissue of a patient.

The introduction of the skin penetrator using the device from FIGS. 1 and 2 proceeds as follows:

A downwardly directed force is applied to the housing upper part 2 and pushes the latter in the direction of the skin, the housing upper part 2 being guided in a sliding movement by the attachment ring 3. This downwardly directed movement of the housing upper part 2, i.e. in the direction of the skin, leads to a lateral displacement of the clip 6 and to rotation of the rotary blade 5. A sharp edge of the rotary blade 5 turns through the opening 10 out of the housing lower part 4, makes an incision in the upper layers of the skin and then turns back to its end position in the housing as far as the abutment 8.

After the rotary blade 5 has made an incision in the skin, the indwelling part 11, for example a sensor for measuring the glucose concentration in the interstitial tissue, is introduced through the opening 10 of the housing lower part 4 and into the subcutaneous tissue. This is achieved by further displacing the housing upper part 2 in the direction of the skin until it has reached its end position. In the end position, the housing upper part 2 and the housing lower part 4 run into one another and, in some preferred embodiments, establish a force-fit connection. The attachment ring 3 can then be removed from the device or falls off.

The indwelling part 11 is arranged in the device in such a way as to pass exactly through the incision made with the rotary blade 5. This arrangement of the indwelling part 11 in the device has the advantage that only a small incision has to be made, i.e. the device according to the invention permits gentle introduction of sensors, for example, into the skin.

Figure 3:
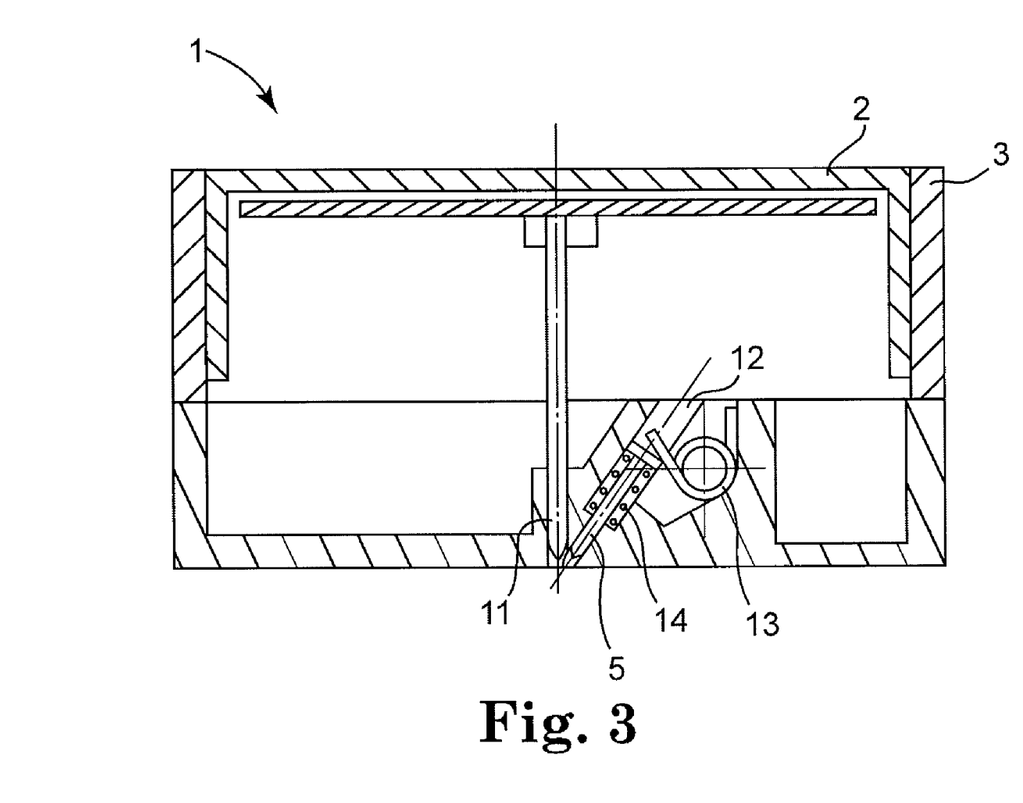
FIG. 3 shows a second embodiment according to the present invention with a puncturing part guided in a translation movement, before use.
Figure 4:
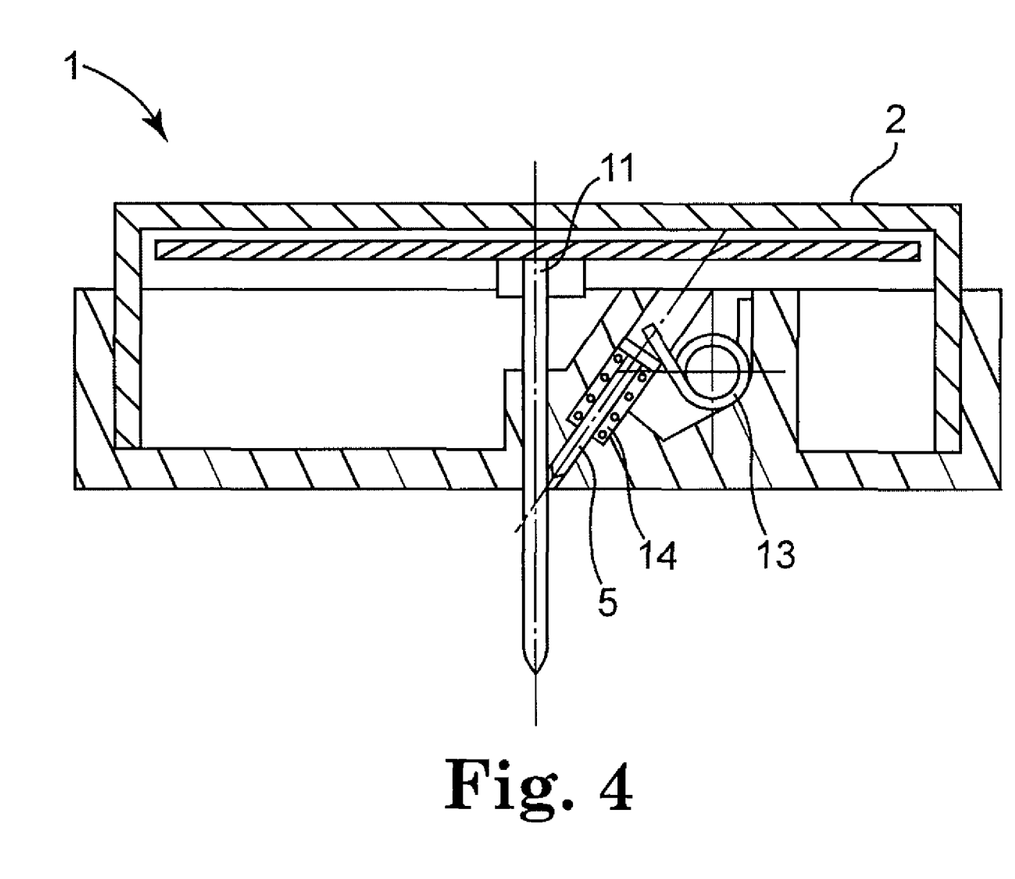
FIG. 4 shows the embodiment of FIG. 3 after its use.

FIG. 3 shows a second embodiment of a device according to the present invention before its use, and FIG. 4 shows the device after introduction of the indwelling part into the subcutaneous tissue of a human, i.e. after its use.

The second embodiment differs from the first embodiment, shown in FIGS. 1 and 2, in terms of the design of the puncturing part 5 which, in the second embodiment, is arranged so as to be linearly displaceable in a guide 12.

The puncturing part 5 is held in the starting position in the guide 12, for example by a pin (not shown). A spring 13 serves as the drive means for displacing the puncturing part 5 in the direction of the surface of the skin. Upon use of the device, the housing upper part 2 is displaced in the direction of the skin, i.e. downward. This downward movement releases the pin, and the puncturing part 5 is introduced into the skin by the tensioned spring 13. The puncturing part 5 is forced forward by the spring 13, until the spring 13 moves into the end position along with the puncturing part 5. At this moment, the retaining spring 14 becomes active and forces the puncturing part 5 back into the starting position. After completed application of the device, the attachment ring 3 can be removed, or it falls off automatically after the application.

Instead of the spring 13 as the drive mechanism or power provider for introduction of the puncturing part 5, it is also possible, for example, to use gas pressure or an elastomer.

FIGS. 5 to 11 show a drive device for introducing the puncturing part of a device according to the present invention. In these drawings, the indwelling part, which is introduced into the skin, is not shown. FIGS. 5, 7, 9 and 11 show a front view of the device, and FIGS. 6, 8, 10 and 12 show a rear view, with adjacent figures showing the same state of the device.

Figure 5:
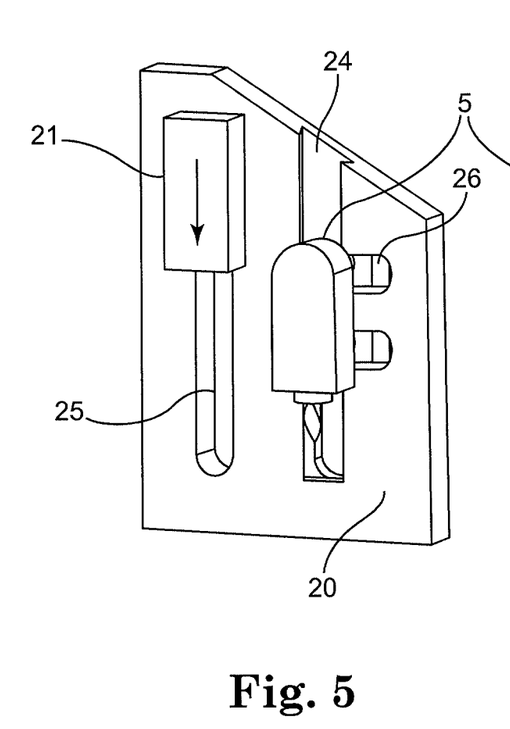
FIG. 5 shows a front view of an example of a drive device for introducing the puncturing part of a device according to the present invention, in a starting position, before introduction of the puncturing part.
Figure 6:
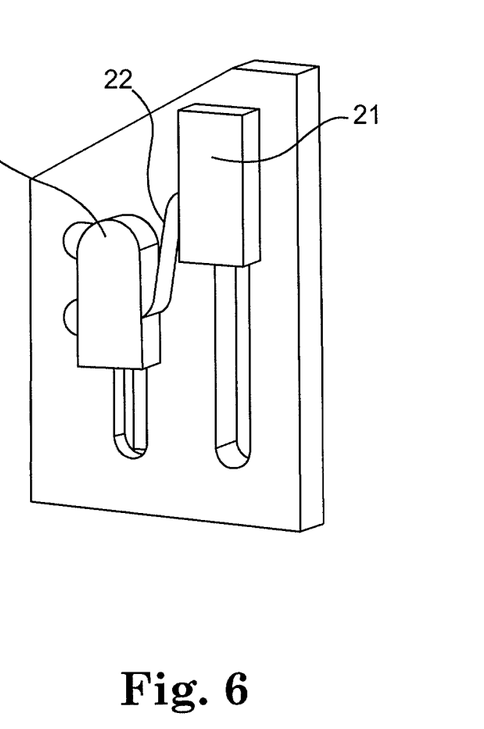
FIG. 6 shows a rear view of the drive device according to FIG. 6.

The drive device comprises a slotted plate 20, a drive element 21 and a puncturing part 5. The drive element 21 is connected by a spring steel sheet 22 to the puncturing part 5, which is guided in an F-shaped slot 24. The slot 24 is characterized by a puncturing part receiver 26 into which the puncturing part 5 is guided after the puncturing procedure has been carried out. The drive element 21 can be driven by a pretensioned draw spring or compression spring or an elastomer band and is guided in the slot 25.

Figure 7:
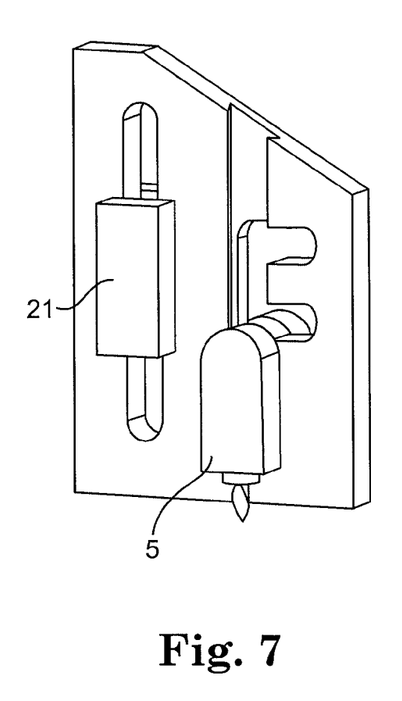
FIG. 7 shows a front view of the drive device according to FIG. 5, with the puncturing part introduced into the skin.
Figure 8:
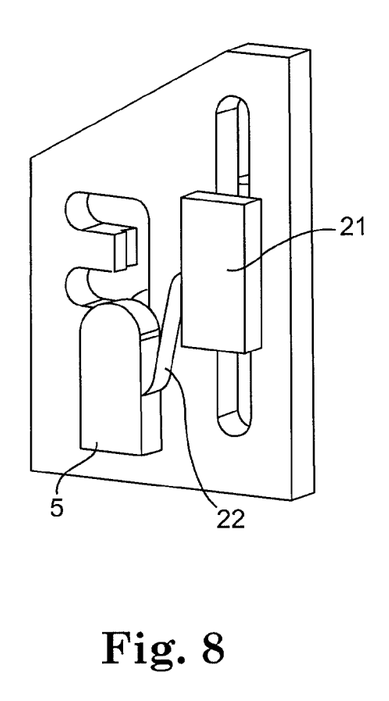
FIG. 8 shows a rear view of the drive device according to FIG. 7.

Referring to FIGS. 7 to 12, the mechanism of the drive device can be described as follows:

The drive element 21 moves downward in the slot 25, i.e. in the direction of the surface of the skin. The puncturing part 5 is carried in the direction of the skin via the spring steel sheet 22 and penetrates the surface of the skin in the lower end position (FIGS. 7 and 8).

Figure 9:
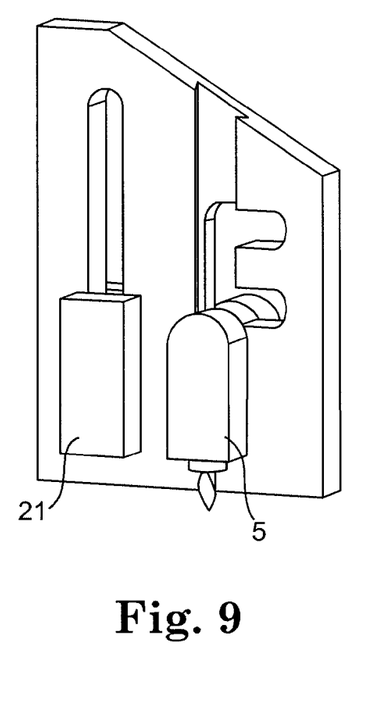
FIG. 9 shows a front view of the drive device according to FIG. 5, with the drive element located in the lower end position.
Figure 10:
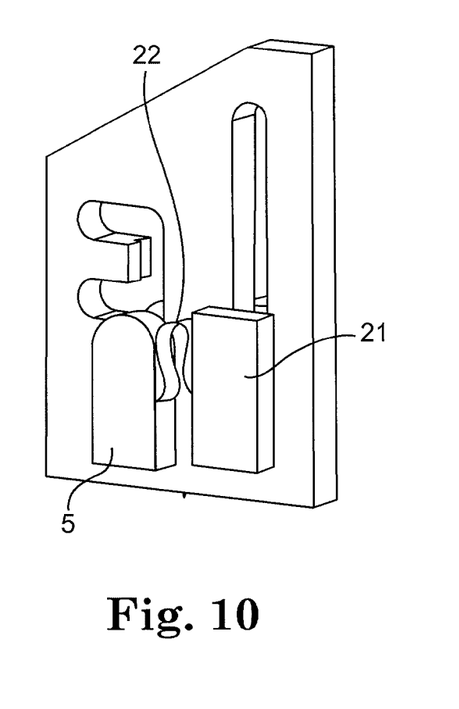
FIG. 10 shows a rear view of the drive device according to FIG. 9.
Figures 11, 12:
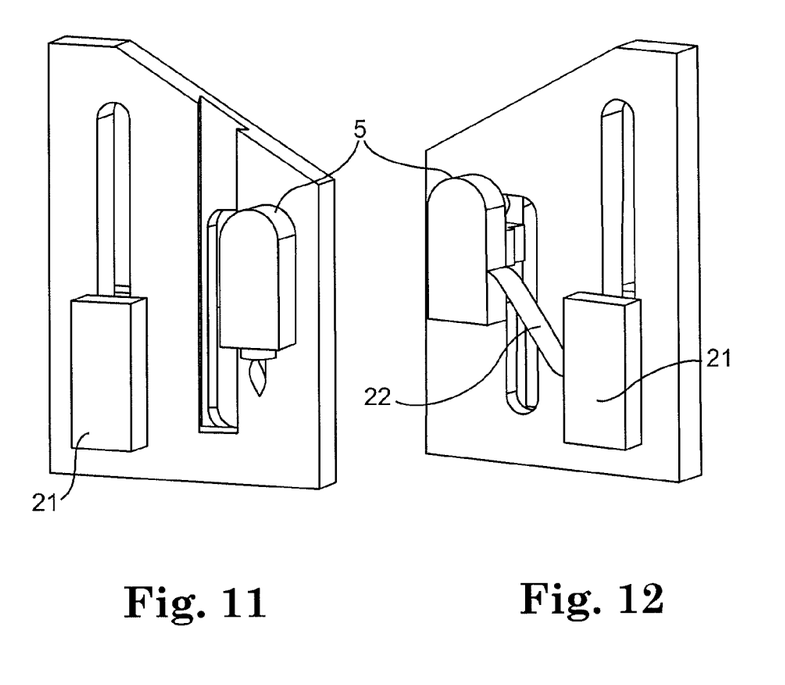
FIG. 11 shows a front view of the drive device according to FIG. 5, with the puncturing part located in the upper end position after retraction from the skin.
FIG. 12 shows a rear view of the device according to FIG. 11.

The drive element 21 moves further in the direction of the surface of the skin and reaches its lower end position (FIGS. 9 and 10). It will be seen from FIG. 10 that, in the lower end position of the drive element 21 and of the puncturing part 5, the spring steel sheet 22 has deformed, i.e. the spring steel sheet is tensioned. The tensioning of the spring steel sheet 22 means that the puncturing part 5 is pushed upward in the slot 24 from its lower end position and deviates sideways into its upper end position (FIGS. 11 and 12).

The lateral deviation of the puncturing part 5 frees the slot 24, in which an indwelling part, for example a sensor, can then be introduced into the skin through the opening created in the skin by the puncturing part 5. The movement of the puncturing part 5 can be coupled to the movement of the indwelling part in such a way that the movement of the indwelling part is triggered as soon as the puncturing part 5 has reached its upper end position.

The spring steel sheet 22 shown in FIGS. 5 to 11 can be replaced, for example, by a leg spring.

Figure 13:
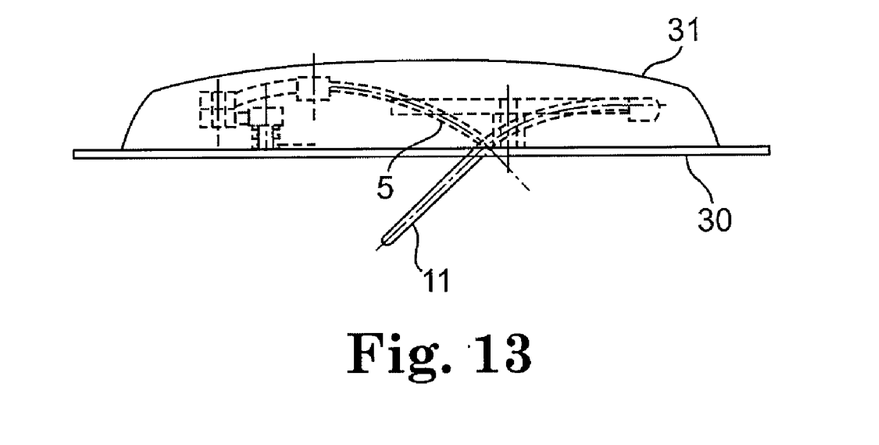
FIG. 13 shows a front view of a device according to the present invention for introduction of skin penetrators, with a puncturing part guided through a curved trajectory.
Figure 14:
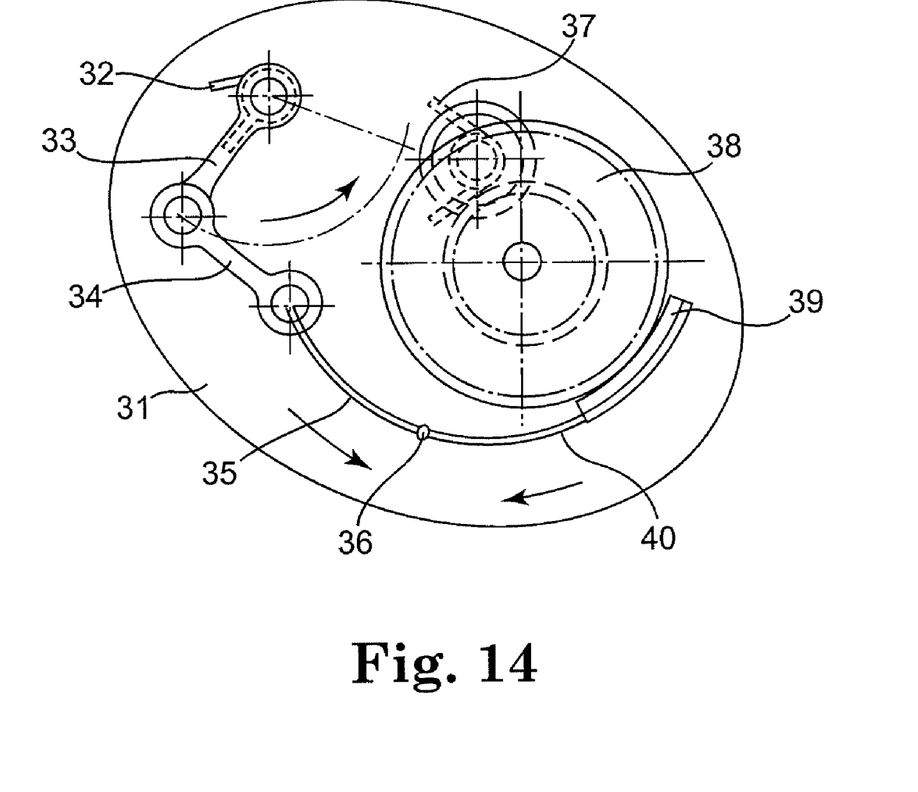
FIG. 14 shows a plan view of the device of FIG. 13.

FIG. 13 depicts a front view of a further embodiment of the present invention, and FIG. 14 shows a plan view of the device. The device is positioned on a patient's skin over a plaster 30.

The device comprises a housing 31, a puncturing part 5, an indwelling part 11 and two interconnected mechanisms, the first mechanism being used to drive the puncturing part 5, i.e. the first mechanism allowing the surface of the skin to be opened by the puncturing part 5. The second mechanism controls the introduction of the indwelling part 11 into the subcutaneous tissue.

The puncturing part 5 is introduced into the skin via a pretensioned leg spring 32, which is driven by two crank arms 33 and 34, and along a curved path 35 integrated in the housing, and it is retracted into the housing after introduction is complete. After the puncturing part 5 has been retracted into the housing 31, a small opening 36 remains in the skin. The indwelling part 11, which is driven by a pretensioned leg spring 37 and a toothed gear 38, is introduced by a guide element 39, and the curved path 40 integrated in the housing, through the skin opening 36 formed by the puncturing part 5 and into the subcutaneous tissue.

The puncturing procedure can be triggered manually by a user, for example via an actuating button (not shown). The subsequent application procedure for introduction of the indwelling part 11 is triggered by the crank arms 33 and 34, i.e. the introduction of the puncturing part and the introduction of the indwelling part are coupled to one another such that the introduction of the indwelling part 11 is triggered after retraction of the puncturing part 5.

Figure 15:
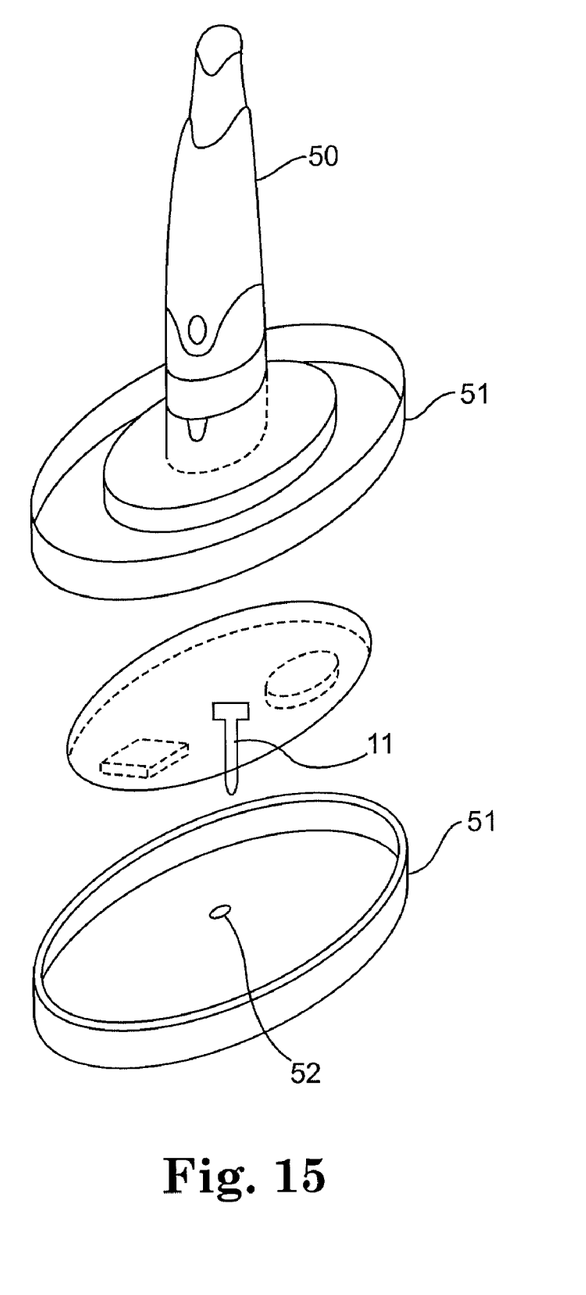
FIG. 15 shows a two-part device for introduction of an indwelling part into tissue.

FIG. 15 shows an embodiment of the present invention in which the puncturing part and the indwelling part are not provided as component parts of one device, but instead are designed as two separate devices. A conventional puncturing aid, such as, for example, those known as the Accu-Check Softclix or Accu-Check Multiclix, can be used as the puncturing device. The indwelling part, for example a sensor, can be integrated in a device that includes, for example, the electronics for controlling the sensor, a data memory, and a telemetry system for transferring data to a third appliance.

In the embodiment of the present invention comprising two separate devices, an embodiment of the method for application of a subcutaneous sensor, for example, is as follows:

A patient arranges a positioning ring 51, for example, on the area of skin where he wishes to apply the sensor. The positioning ring 51 has, for example, a planar underside, with an opening 52 through which the puncturing part 5 of the puncturing device 50 is introduced, and a circumferential surface. To ensure that the positioning ring 51 adheres to the surface of the skin, it has a plaster or adhesive, for example, on its underside. The puncturing device 50 is then fitted into the ring and fixed releasably therein, to permit precise piercing of the skin. The puncturing device 50 can be fixed in place via the circumferential surface of the ring, for example.

The patient then carries out the puncturing procedure and releases the puncturing device 50 from the positioning ring 51 after the puncturing procedure has been completed. He then introduces the sensor, for example, of the indwelling device through the opening in the skin and fixes the indwelling device on the positioning ring. After use, the indwelling device is removed with the positioning ring from the surface of the skin and is disposed of.

Figure 16:
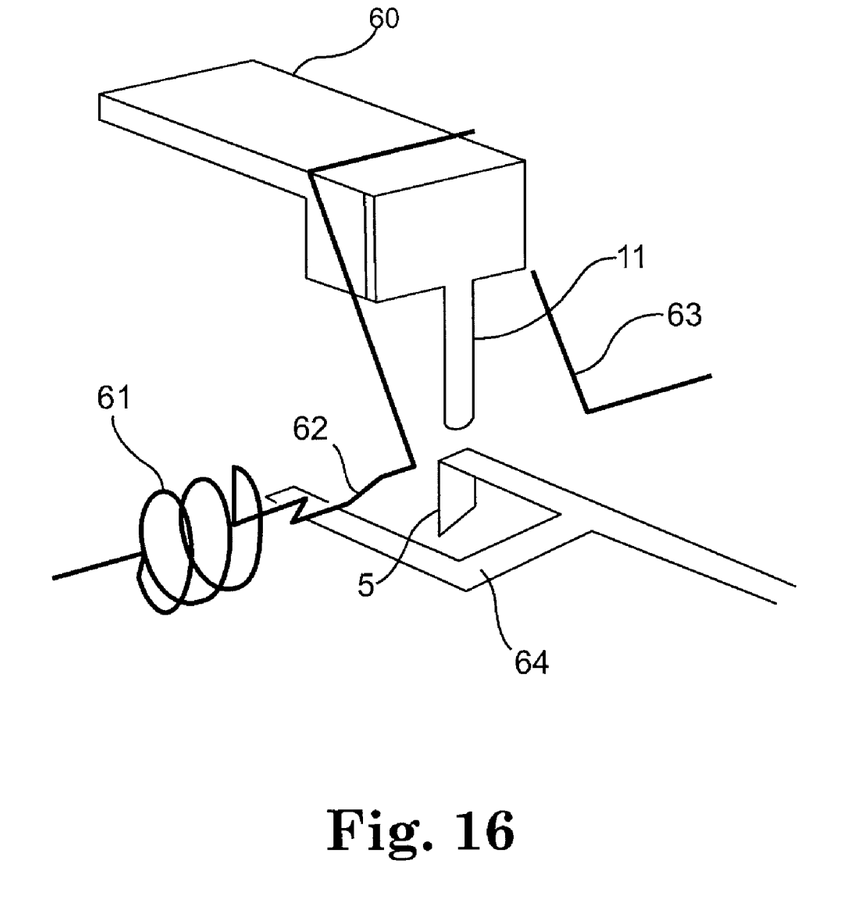
FIG. 16 is a three-dimensional depiction of an embodiment of a sequential device in accordance with the present invention, the device being for introduction of skin penetrators.

FIG. 16 shows another example of a device for sequential introduction of an indwelling part 11 in accordance with the present invention. The device comprises a vertically guided base plate 60, a drive device 61, 62, 63, and a puncturing part 5.

The drive device comprises a spring steel wire, which is bent at one location into a helical spring 61 and has clips 62, 63 which protrude at two locations and which act sequentially on the puncturing part 5 and on the indwelling part 11.

The clips 62 and 63 are mutually offset by 90°, such that the clip 62 first presses the puncturing part 5 down via a clip 64, after which the clip 63 presses the indwelling part 11 down via a force acting on the base plate 60. During the insertion procedure, the clips 62 and 63 turn through almost 180°. The angle offset has the effect that the clip 62 executes a vertical downward movement followed by an upward movement, while the clip 63 moves exclusively downward in the vertical direction.

The described procedure can also be realized using two offset cam discs that are coupled to a drive.

In an alternative design, the clip 63 does not act as a drive, but instead as inhibitor on the base plate 60, which in this case is driven downward by an external drive (not shown).

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for application of skin penetrators, the device comprising:
   a housing comprising a housing underside for contacting the skin, the housing underside having one or more openings therein;
   a puncturing part for piercing the skin;
   an indwelling part which can be introduced into the skin through an opening in the skin generated by the puncturing part and remains there;
   a guide associated with the device; and
   an elastic drive device adapted to drive the puncturing part into the skin;
   wherein, in use, the indwelling part and the puncturing part are introduced into the skin sequentially such that the indwelling part is moved through one of the one or more openings in the housing underside after the puncturing part is moved through one of the one or more openings in the housing underside.

2. The device according to claim 1, wherein the puncturing part and the indwelling part are separate from each other and the device prior to use.

3. The device according to claim 1, wherein the housing carries the guide.

4. The device according to claim 3, wherein the guide comprises an abutment for contact by at least one of the puncturing part and the indwelling part, the abutment forming a hold point for at least one of the puncturing part and the indwelling part, wherein the puncturing part and the indwelling part are guided in the guide in an operable movement that brings the puncturing part into contact with the abutment thereby holding the puncturing part at the hold point, the operable movement then continuing to move the indwelling part into an indwelling use position.

5. A device for use in the use of skin penetrators, the device comprising a puncturing part, which pierces the skin to define an opening therein, an indwelling part, and an elastic drive device adapted to drive the puncturing part into the skin, wherein the indwelling part moves from an initial position to an indwelling position in which it is introduced into the skin through the opening generated by the puncturing part, wherein the puncturing part and indwelling part are provided separately on the device, and wherein the indwelling part moves relative to the puncturing part during movement from the initial position to the indwelling position, and at least one guide in or on which, after the puncturing part, the indwelling part is introduced into the skin through the opening.

6. The device according to claim 5, further comprising a housing in or on which the puncturing part and the indwelling part are arranged.

7. The device according to claim 6, further comprising a guide whereby the puncturing part and the indwelling part are introduced into the skin through the guide.

8. The device according to claim 7, further comprising a retaining member associated with the guide, said retaining member at least one of retaining the puncturing part in the retracted position and holding the coupled puncturing part and indwelling part in the in-use position of the indwelling part.

9. The device according to claim 7, further comprising a puncturing part receiver associated with at least one of the guide or the housing to receive and hold the puncturing part, after the puncturing part is moved from the puncture position.

10. The device according to claim 7, wherein the guide has a hold point assigned to at least one of a puncture position or an in-use position.

11. The device according to claim 10, wherein the hold point is formed by an abutment for at least one of the puncturing part and the indwelling part.

12. The device according to claim 11, wherein the puncturing part and the indwelling part are guided in the guide in a coupled movement, and the hold point is generated by an abutment onto which the puncturing part is guided after the puncturing procedure, thereby carrying the indwelling part into the in-use position.

13. The device according to claim 11, wherein the puncturing part and the indwelling part are received in a housing in which the guide and the abutment are accommodated, and the housing has a passage for the puncturing part and the indwelling part.

14. The device according to claim 10, wherein the hold point is formed by a locking engagement for the puncturing part and the indwelling part, the locking engagement being arranged in or on the guide.

15. The device according to claim 14, wherein a single releasable locking engagement is provided in or on the guide, into which first the puncturing part and thereafter the indwelling part can lock.

16. The device according to claim 5, wherein the puncturing part and the indwelling part are guided through different guides.

17. The device according to claim 5, wherein the guide is one of a curved guide, a linear guide or a combination curved and linear guide.

18. The device according to claim 5, wherein the indwelling part is made of a material that has a greater stiffness at ambient or room temperature than it does at body temperature.

19. The device according to claim 5, wherein the indwelling part is a sensor for measuring a physiological parameter.

20. The device according to claim 19, wherein the physiological parameter interstitial glucose concentration.

21. A device for application of skin penetrators, the device comprising:
   a puncturing part for piercing the skin, wherein the puncturing part moves from an initial position to a puncturing position in which the puncturing part pierces the skin to define an opening therein, and from the puncturing position to a post-puncturing position in which the puncturing part is removed from the opening;
   an indwelling part, wherein the indwelling part moves from an initial position to an indwelling position in which it is introduced into the skin through the opening generated by the puncturing part, wherein the puncturing part and indwelling part are spaced-apart from each other substantially throughout their respective movements into the skin, and the indwelling part moves relative to the puncturing part during movement from the initial position to the indwelling position;
   a housing in or on which the puncturing part and the indwelling part are arranged, wherein in the initial position a distal end of the indwelling part is disposed above a bottom surface of the housing, and in the indwelling position the distal end of the indwelling part is disposed below the bottom surface of the housing;
   a guide associated with the device, wherein the indwelling part is moved in or onto the guide after the puncturing part is moved in or onto the guide; and
   an elastic drive device adapted to drive the puncturing part into the skin.

22. A device for application of skin penetrators, the device comprising:
- a housing comprising a housing underside for contacting the skin, the housing underside having one or more openings therein;
- a puncturing part for piercing the skin;
- an indwelling part which can be introduced into the skin through an opening in the skin generated by the puncturing part and remains there,
- a guide associated with the device, the guide comprising a guide slot for guiding the piercing part and the indwelling part into the skin and a receiver slot adapted to receive the puncturing part after its puncturing movement, wherein the receiver slot extends at an angle relative to the guide slot; and
- wherein, in use, the indwelling part and the puncturing part are introduced into the skin sequentially such that the indwelling part is moved through the guide slot and one of the one or more openings in the housing underside after the puncturing part is moved through the guide slot and one of the one or more openings in the housing underside.

23. The device according to claim 22, further comprising an elastic drive device adapted to drive the puncturing part into the skin.

24. The device according to claim 23, wherein the guide slot and the receiver slot form a continuous path.

* * * * *